United States Patent
Mansfield et al.

(10) Patent No.: US 7,524,968 B2
(45) Date of Patent: Apr. 28, 2009

(54) 2-PYRIDINYLCYCLOALKYLBENZAMIDE DERIVATIVES AND THEIR USE AS FUNGICIDES

(75) Inventors: Darren James Mansfield, Lyons (FR); Pierre-Yves Coqueron, Lyons (FR); Philippe Desbordes, Lyons (FR); Heiko Rieck, Sainte-Foy-lés-Lyon (FR); Marie-Claire Grosjean-Cournoyer, Curis Au Mont d'Or (FR); Pierre Genix, Lyons (FR); Alain Villier, Saint Cyr Au Mont d'Or (FR)

(73) Assignee: Bayer Cropscience S.A. (FR)

( * ) Notice: Subject to any disclaimer, the term of this patent is extended or adjusted under 35 U.S.C. 154(b) by 38 days.

(21) Appl. No.: 11/587,908

(22) PCT Filed: Apr. 25, 2005

(86) PCT No.: PCT/EP2005/005800

§ 371 (c)(1), (2), (4) Date: Dec. 29, 2006

(87) PCT Pub. No.: WO2005/103004

PCT Pub. Date: Nov. 3, 2005

(65) Prior Publication Data

US 2007/0203204 A1     Aug. 30, 2007

(30) Foreign Application Priority Data

Apr. 26, 2004   (EP) .................................. 04356056

(51) Int. Cl.
    C07D 211/72   (2006.01)
(52) U.S. Cl. ..................................................... 546/345
(58) Field of Classification Search ................. 546/345
    See application file for complete search history.

(56) References Cited

FOREIGN PATENT DOCUMENTS

| WO | WO 99/42447 | 8/1999 |
|---|---|---|
| WO | WO 01/11965 | 2/2001 |
| WO | WO 2004/016088 | 2/2004 |
| WO | WO/2004/016088 | * 2/2004 |

* cited by examiner

*Primary Examiner*—D. Margaret Seaman
*Assistant Examiner*—Nizal S Chandrakumar
(74) *Attorney, Agent, or Firm*—Ostrolenk, Faber, Gerb & Soffen, LLP

(57) ABSTRACT

A compound of general formula (I):

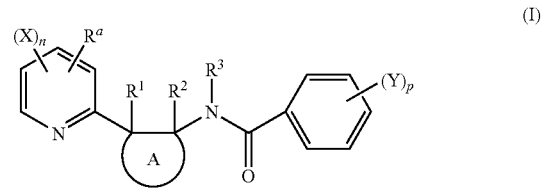

A process for preparing this compound.

A fungicidal composition comprising a compound of general formula (I).

A method for treating plants by applying a compound of general formula (I) or a composition comprising it.

12 Claims, No Drawings

2-PYRIDINYLCYCLOALKYLBENZAMIDE DERIVATIVES AND THEIR USE AS FUNGICIDES

CROSS REFERENCE TO RELATED APPLICATION(S)

The present application is a 35 U.S.C. § 371 national phase conversion of PCT/EP2005/005800 filed Apr. 25, 2005, which claims priority of European Application No. 04356056.4 filed Apr. 26, 2004.

The present invention relates to novel N-[2-(2-pyridinyl)cycloalkyl]benzamide derivatives, their process of preparation, their use as fungicides, particularly in the form of fungicidal compositions, and methods for the control of phytopathogenic fungi of plants using these compounds or their compositions.

International patent application WO 01/11965 discloses a broad family of fungicidal compounds. There is no specific disclosure of N-[2-(2-pyridinyl)cycloalkyl]benzamide derivatives.

It is always of high-interest in the field of agrochemicals to use pesticidal compounds more active than the compounds already known by the man ordinary skilled in the art whereby less compound can be used whilst retaining equivalent efficacy.

We have now found a new family of compounds which show enhanced fungicidal activity over the general known family of such compounds.

Accordingly, the present invention relates to a N-[2-(2-pyridinyl)cycloalkyl]benzamide derivative of general formula (I)

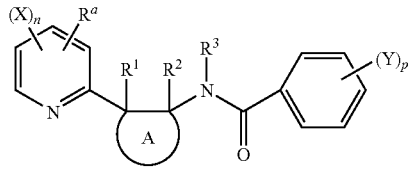

(I)

in which:
n is 1, 2, or 3;
p is 1, 2, 3, 4 or 5;
$R^a$ is a $C_1$-$C_6$-halogenoalkyl having 1 to 5 halogen atoms;
each substituent X is chosen, independently of the others, as being a hydrogen atom, a halogen atom, a $C_1$-$C_6$-alkyl or a $C_1$-$C_6$-halogenoalkyl;
A is a 3-, 4-, 5-, 6- or 7-membered non aromatic carbocycle;
$R^1$ and $R^2$ are chosen, independently of each other, as being a hydrogen atom, a halogen atom, a cyano group, a hydroxy group, an amino group, a sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a (N—$C_1$-$C_6$-alkyl)oxycarbamoyl, a $C_1$-$C_6$-alkoxycarbamoyl, a (N—$C_1$-$C_6$-alkyl)-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulphenyl, a $C_1$-$C_6$-halogenoalkylsulphenyl having 1 to 5 halogen atoms, a $C_1$-$C_6$-alkylsulphinyl, a $C_1$-$C_6$-halogenoalkylsulphinyl having 1 to 5 halogen atoms, a $C_1$-$C_6$-alkylsulphonyl, a $C_1$-$C_6$-halogenoalkylsulphonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group or a phenyl group,
$R^3$ is chosen as being a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms; and
each substituent Y is chosen, independently of the others, as being a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;
as well as its salts, N-oxides, metallic complexes, metalloidic complexes and optically active isomers.

In the context of the present invention:
halogen means fluorine, bromine, chlorine or iodine.
carboxy means —C(═O)OH; carbonyl means —C(═O)—; carbamoyl means —C(═O)NH$_2$; N-hydroxycarbamoyl means —C(═O)NHOH;

an alkyl group, an alkenyl group, and an alkynyl group as well as moieties containing these terms, can be linear or branched.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compound of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compound of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compound of general formula (I) wherein $R_1$ represents a hydroxy or sulfanyl group, and/or X represents a hydroxy, sulfanyl or amino group, may be found in its tautomeric form resulting of the shift of the proton of said hydroxy, sulfanyl or amino group. Such tautomeric forms of such compounds are also part of the present invention. More generally speaking, all tautomeric forms of compounds of general formula (I) wherein $R_1$ represents a hydroxy or sulfanyl group, and/or X represents a hydroxy, sulfanyl or amino group, as well as the tautomeric forms of the compounds which can optionally be used as intermediates in the preparation processes, and which will be defined in the description of these processes, are also part of the present invention.

According to the present invention, the 2-pyridyl may be substituted in every position by $(X)_n$ and $R^a$, in which $X$, $R^a$ and n are as defined above. Preferably, the present invention relates to N-[2-(2-pyridinyl)cycloalkyl]benzamide derivative of general formula (I) in which the different characteristics may be chosen alone or in combination as being:

as regards n, n is 1 or 2. More preferably n is 1.
as regards X, X is preferably chosen as being a halogen atom. More preferably X is chlorine;
as regards $R^a$, $R^a$ is preferably chosen as being —CF$_3$;
as regards the positions in which the 2-pyridyl is substituted, the 2-pyridyl is substituted in 3- and/or in 5-position. More preferably, the 2-pyridyl is substituted in 3-position by X and in 5-position by $R^a$.

Even more preferably, the 2-pyridyl is substituted in 3-position by —Cl and in 5-position by —CF$_3$.

According to the present invention, A is a 3-, 4-, 5-, 6- or 7-membered non aromatic carbocycle. Preferably, A is a 3-, 5-, 6- or 7-membered non aromatic carbocycle. Even more preferably, A is chosen from cyclopropyl, cyclopentyl, cyclohexyl and cycloheptyl.

According to the present invention, the phenyl group is substituted in any position by $(Y)_p$, in which Y and p are as defined above. Preferably, the present invention relates to N-[2-(2-pyridinyl)cycloalkyl]benzamide derivative of general formula (I) in which the different characteristics may be chosen alone or in combination as being:

as regards p, p is 1 or 2;
as regards Y, Y is a hydrogen atom, a halogen atom, a $C_1$-$C_6$-alkyl, a $C_1$-$C_6$-alkoxy or a $C_1$-$C_6$-halogenoalkyl having 1 to 5 halogen atoms;
as regards the positions in which the phenyl moiety is substituted by Y, the phenyl moiety is substituted by Y preferentially first in ortho position.

According to the present invention, two of the carbon atoms of the cycloalkyl moiety of the compound of formula (I) are respectively substituted by $R^1$ and $R^2$. Preferably, the present invention also relates to N-[2-(2-pyridinyl)cycloalkyl]benzamide derivative of general formula (I) in which $R^1$ and $R^2$ may be chosen, independently of each other, as being a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonylamino, a $C_1$-$C_6$-alkoxycarbonyloxy, a $C_1$-$C_6$-alkoxycarbonylamino or a phenyl group. More preferably, $R^1$ and $R^2$ may be chosen, independently of each other, as being a hydrogen atom, a halogen atom, a $C_1$-$C_6$-alkyl, a $C_1$-$C_6$-halogenoalkyl having 1 to 5 halogen atoms or a $C_1$-$C_6$-alkylcarbonylamino. Even more preferably, $R^1$ and $R^2$ are both a hydrogen atom.

According to the present invention, the nitrogen atom of the carboxamide moiety of the compound of formula (I) is substituted by $R^3$, $R^3$ being as defined above. Preferably, the present invention also relates to N-[2-(2-pyridinyl)cycloalkyl]benzamide derivative of general formula (I) in which $R^3$ may be chosen as being a hydrogen atom or a $C_3$-$C_7$-cycloalkyl. Even more preferably, the $C_3$-$C_7$-cycloalkyl is cyclopropyl.

The present invention also relates to a process for the preparation of the compound of general formula (I). Thus, according to a further aspect of the present invention there is provided a process for the preparation of compound of general formula (I) as defined above, which comprises reacting a 2-pyridine derivative of general formula (II) or one of its salt:

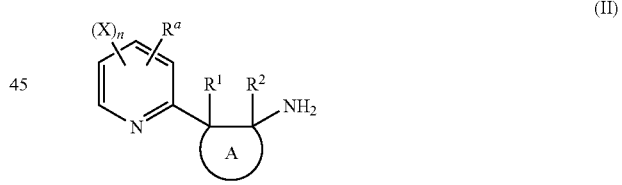

(II)

in which X, Y, n, p, $R^a$, $R^1$, $R^2$ and A are as defined above; with a carboxylic acid derivative of the general formula (III)

(III)

in which:
$L^1$ is a leaving group chosen as being a halogen atom, a hydroxyl group, —OR$^7$, —OCOR$^7$, R$^7$ being a $C_1$-$C_6$ alkyl, a $C_1$-$C_6$ haloalkyl, a benzyl, 4-methoxybenzyl, pentafluorophenyl or a group of formula

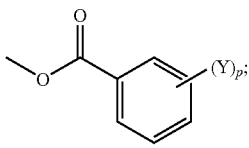

in the presence of a catalyst and, if $L^1$ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case $L^1$ is a hydroxy group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

When $R^3$ in the desired product is not a hydrogen atom, the above mentioned process for the preparation of compound of general formula (I) may optionally be completed by a further step according to the following reaction scheme:

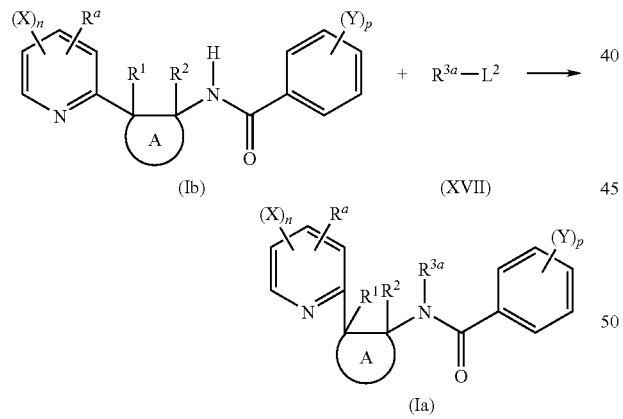

in which:
$R^1$, $R^2$, A, $R^a$, X, Y, n and p are as defined above;
$R^{3a}$ is chosen as being a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms; and
$L^2$ is a leaving group chosen as being a halogen atom, a 4-methyl phenylsulfonyloxy or a methylsulfonyloxy;

comprising the reaction of a compound of general formula (Ib) with a compound of general formula (XVII) to provide a compound of general formula (Ia).

Depending on the definition of A, $R^1$, $R^2$, $R^3$, amine derivatives of general formula (II) may be prepared by different processes. One example (a) of such a process may be when:

$R^1$, $R^2$, A, $R^a$, X, n are as defined above;
$R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;

then, the amine derivative of general formula (II) may be prepared according to a process comprising:
a first step according to reaction scheme a-1:

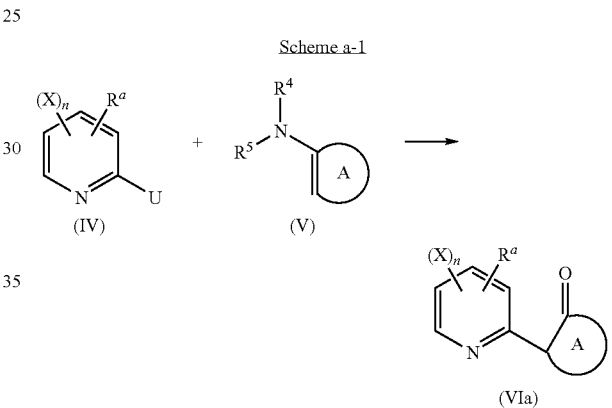

in which:
$R^a$, A, X and n are as defined above;
$R^4$ and $R^5$ are a $C_1$-$C_6$ alkyl or may form a 5-, 6- or 7-membered carbocyclic or heterocyclic ring;
U is a leaving group chosen as being a halogen, a $C_1$-$C_6$ alkylsulfonate or a $C_1$-$C_6$ haloalkylsulfonate;

comprising the arylation of an enamine derivative of general formula (V) by a pyridine derivative of general formula (IV), to provide a 2-(pyridyl)ketone derivative of general formula (VIa), at a temperature of from 0° C. to 200° C.;
a second step according to reaction scheme a-2:

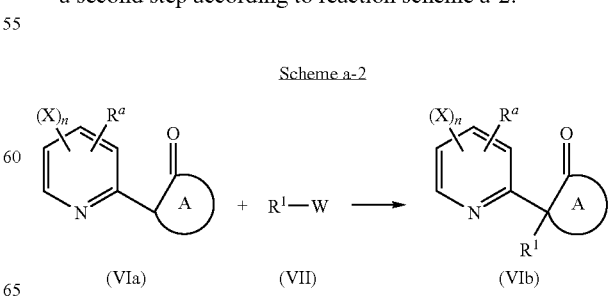

in which:

$R^a$, A, X and n are as defined above;

$R^1$ is a $C_1$-$C_6$ alkyl;

W is a halogen atom, a $C_1$-$C_6$ alkylsulfonate, a $C_1$-$C_6$ haloalkylsulfonate or a 4-methyl-phenylsulfonate, comprising the alkylation of a compound of general formula (VIa) by a reagent of general formula (VII) to provide a compound of general formula (VIb);

a third step according to reaction scheme a-3:

Scheme a-3

(VIa) ou (VIb) → (VIII)

in which:

$R^a$, A, X and n are as defined above;

$R^1$ is a hydrogen atom or a $C_1$-$C_6$ alkyl;

$R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;

comprising the reaction of a compound of general formula (VIa) or (VIb) with an amine of formula $R^3$—NH2 to provide an imine derivative of general formula (VIII);

a fourth step according to scheme a-4:

Scheme a-4

(VIII) → (IIa)

in which:

$R^a$, A, X and n are as defined above;

$R^1$ is a hydrogen atom, a $C_1$-$C_6$ alkyl, $R^3$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;

comprising the reduction of an imine derivative of general formula (VIII) by hydrogenation or by an hydride donor, in the same or a different pot to provide an amine derivative of general formula (IIa) or one of its salt.

A second example (b) of such a process may be when:

$R^a$, $R^2$, $R^3$, A, X and n are as defined above;

$R^1$ is a hydrogen atom;

then, the amine derivative of general formula (II) may be prepared according to a process comprising:

a first step according to reaction scheme b-1:

Scheme b-1

(IV) + (IX) → (X)

in which:

$R^a$, $R^2$, A, X and n are as defined above;

U is a leaving group chosen as being a halogen, a $C_1$-$C_6$ alkylsulfonate or a $C_1$-$C_6$ haloalkylsulfonate;

M is a metal or a metalloid specie;

comprising a coupling reaction of a pyridine derivative of general formula (IV) with a vinylic specie of general formula (IX), at a temperature of from 0° C. to 200° C., to provide a compound of general formula (X);

a second step according to reaction scheme b-2:

Scheme b-2

(X) → (XI)

in which $R^a$, $R^2$, A, X and n are as defined above;

comprising the addition of a phtalimide or one of its salt on a compound of general formula (X) to provide a compound of general formula (XI);

a third step according to reaction scheme b-3:

Scheme b-3

(XI) → (IIb)

in which $R^a$, $R^2$, A, X and n are as defined above;

comprising the de-protection of a compound of general formula (XI) with hydrazine hydrate or an hydrazine salt, to provide an amine derivative of general formula (IIb) or one of its salts.

The first step (step b-1) of the process b according to the present invention is conducted in the presence of a vinylic specie of general formula (IX) in which M can be a metal or a metalloid specie. Preferably M is a tin derivative or a boron derivative. More preferably M is a tri-nbutyltin group.

The first step (step b-1) of the process b according to the present invention is conducted at a temperature of from 0° C. to 200° C.

The first step (step b-1) of the process b according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step b-1) of the process b according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyldicyclohexylphosphine and its corresponding enantiomer, or a mixture of both; (R)-(–)-1[(S)-2-(dicyclohexylphosphino)ferrocenyl]ethyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The first step (step b-1) of the process b according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

A third example (c) of such a process may be when:
$R^a$, $R^1$, X, n are as defined above;
$R^2$, $R^3$ are a hydrogen atom
A is a cyclopropyl ring;

then, the amine derivative of general formula (II) may be prepared according to a process comprising:
a first step according to reaction scheme c-1:

Scheme c-1

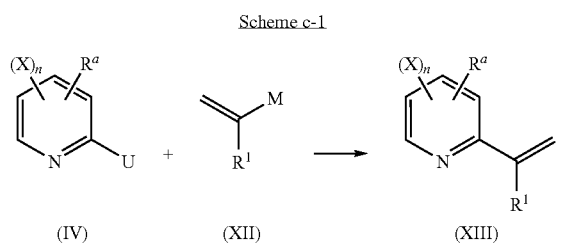

(IV)    (XII)    (XIII)

in which:
$R^a$, $R^1$, X, n are as defined above;
U is a leaving group chosen as being a halogen, a $C_1$-$C_6$ alkylsulfonate or a $C_1$-$C_6$ haloalkylsulfonate;
M is a metal or a metalloid specie;

comprising a coupling reaction of a pyridine derivative of general formula (IV) with a vinylic specie of general formula (XII), at a temperature of from 0° C. to 200° C., to provide a compound of general formula (XIII);

a second step according to reaction scheme c-2:

Scheme c-2

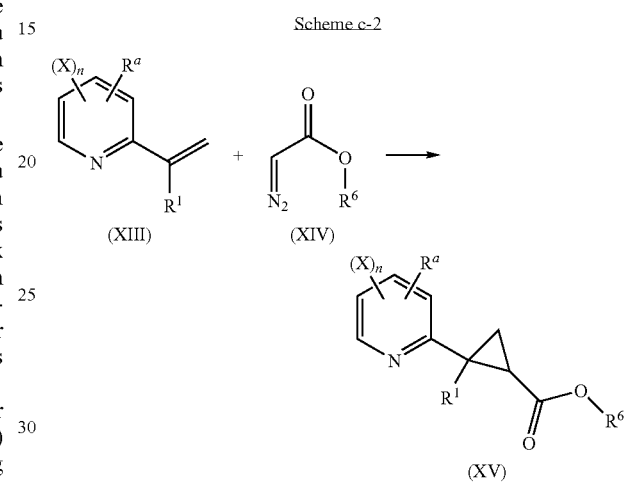

in which:
$R^a$, $R^1$, X and n are as defined above;
$R^6$ is a $C_1$-$C_6$ alkyl group;

comprising a cyclopropanation reaction of a vinylic pyridine derivative of general formula (XIII) with a diazo specie of general formula (XIV), at a temperature of from 0° C. to 200° C., to provide a compound of general formula (XV);

a third step according to reaction scheme c-3:

Scheme c-3

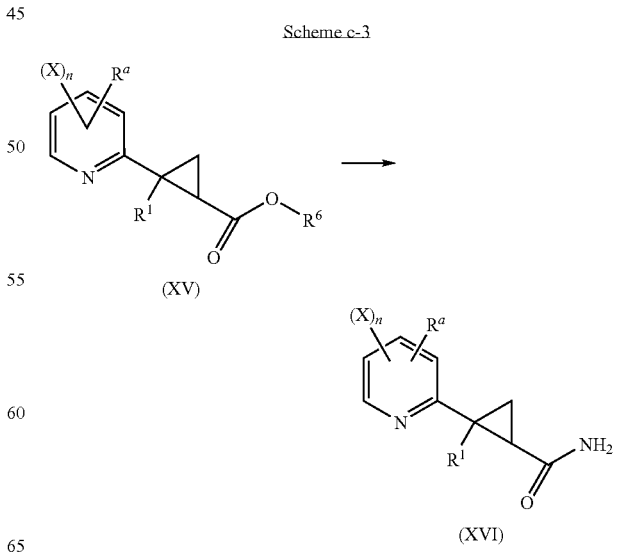

in which:

$R^a$, $R^1$, X and n are as defined above;
$R^6$ is a $C_1$-$C_6$ alkyl group;

comprising an amidification reaction of a ester derivative of general formula (XV) to provide a compound of general formula (XVI);

a fourth step according to reaction scheme c-4:

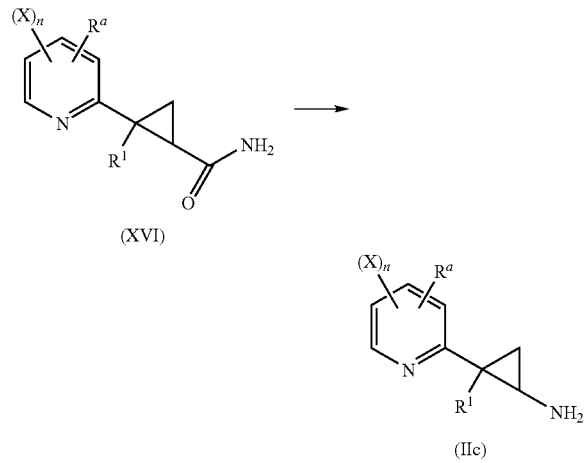

in which $R^a$, $R^1$, X and n are as defined above;

comprising a rearrangement reaction of a primary amide derivative of general formula (XVI) in presence of a halogenating agent, to provide an amine of general formula (IIc).

The first step (step c-1) of the process c according to the present invention is conducted in the presence of a vinylic specie of general formula (XII) in which M can be a metal or a metalloid specie. Preferably M is a tin derivative or a boron derivative. More preferably M is a tri-nbutyltin group.

The first step (step c-1) of the process c according to the present invention is conducted at a temperature of from 0° C. to 200° C.

The first step (step c-1) of the process c according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step c-1) of the process c according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyldicyclohexylphosphine and its corresponding enantiomer, or a mixture of both; (R)-(–)-1[(S)-2-(dicyclohexylphosphino)ferrocenyl]ethyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The first step (step c-1) of the process c according to the present invention may also be conducted in the presence of a base. Preferably, the base is chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

Compounds according to the present invention can be prepared according to the above described processes. It will nevertheless be understood that, on the basis of his general knowledge and of available publications, the skilled worker will be able to adapt these processes according to the specifics of each of the compounds which it is desired to synthesize.

The compound of general formula (II) used as an intermediate for the preparation of compound of general formula (I) is novel. Therefore, the present invention also relates to novel intermediate compound useful for the preparation of compound of general formula (I). Thus, according to the present invention, there is provided a compound of general formula (II):

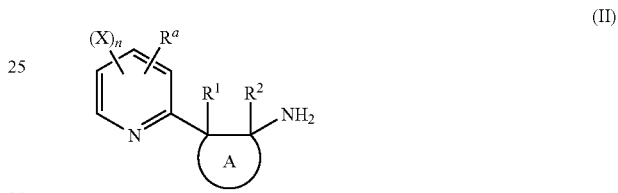

in which X, n, $R^a$, $R^1$, $R^2$ and A are as defined above.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilizers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilizers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterized in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantains),*Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces),*Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* forma specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* forma specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes), fusaria (Fusarium oxysporum), grey mould (Botrytis cinerea) and mildew (Peronospora pisi);

oil-bearing crops, for example rape, as regards controlling the following seed diseases: Phoma lingam, Alternaria brassicae and Sclerotinia sclerotiorum;

corn, as regards controlling seed diseases: (Rhizopus sp., Penicillium sp., Trichoderma sp., Aspergillus sp., and Gibberella fujikuroi);

flax, as regards controlling the seed disease: Alternaria linicola;

forest trees, as regards controlling damping-off (Fusarium oxysporum, Rhizoctonia solani);

rice, as regards controlling the following diseases of the aerial parts: blast disease (Magnaporthe grisea), bordered sheath spot (Rhizoctonia solani);

leguminous crops, as regards controlling the following diseases of seeds or of young plants grown from seeds: damping-off and collar rot (Fusarium oxysporum, Fusarium roseum, Rhizoctonia solani, Pythium sp.);

leguminous crops, as regards controlling the following diseases of the aerial parts: grey mould (Botrytis sp.), powdery mildews (in particular Erysiphe cichoracearum, Sphaerotheca fuliginea and Leveillula taurica), fusaria (Fusarium oxysporum, Fusarium roseum), leaf spot (Cladosporium sp.), alternaria leaf spot (Alternaria sp.), anthracnose (Colletotrichum sp.), septoria leaf spot (Septoria sp.), black speck (Rhizoctonia solani), mildews (for example Bremia lactucae, Peronospora sp., Pseudoperonospora sp., Phytophthora sp.);

fruit trees, as regards diseases of the aerial parts: monilia disease (Monilia fructigenae, M. laxa), scab (Venturia inaequalis), powdery mildew (Podosphaera leucotricha);

vine, as regards diseases of the foliage: in particular grey mould (Botrytis cinerea), powdery mildew (Uncinula necator), black rot (Guignardia biwelli) and mildew (Plasmopara viticola);

beetroot, as regards the following diseases of the aerial parts: cercospora blight (Cercospora beticola), powdery mildew (Erysiphe beticola), leaf spot (Ramularia beticola).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, trichophyton diseases and candidiases or diseases caused by Aspergillus spp., for example Aspergillus fumigatus.

The aspects of the present invention will now be illustrated with reference to the following tables of compounds and examples. The following Tables A to V illustrate in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy.

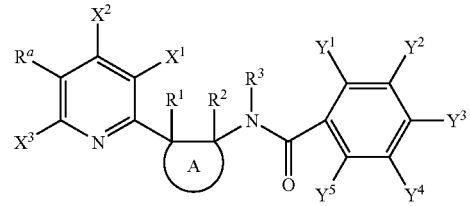

(I)

| Compound | $R^a$ | $X^1$ | $X^2$ | $X^3$ | A | $R^1$ | $R^2$ | $R^3$ | $Y^1$ | $Y^2$ | $Y^3$ | $Y^4$ | $Y^5$ | M + 1 |
|---|---|---|---|---|---|---|---|---|---|---|---|---|---|---|
| 1 | $CF_3$ | Cl | H | H | Cis-cyclohexyl | H | H | H | $CF_3$ | H | H | H | H | 451 |
| 2 | $CF_3$ | Cl | H | H | Trans-cyclohexyl | H | H | H | $CF_3$ | H | H | H | H | 451 |
| 3 | $CF_3$ | Cl | H | H | Cyclohexyl | H | H | H | $CHF_2$ | H | H | H | H | 433 |
| 4 | $CF_3$ | Cl | H | H | Cis-cyclohexyl | H | H | H | I | H | H | H | H | 509 |
| 5 | $CF_3$ | Cl | H | H | Trans-cyclohexyl | H | H | H | I | H | H | H | H | 509 |
| 6 | $CF_3$ | Cl | H | H | Cycloheptyl | H | H | H | $CF_3$ | H | H | H | H | 424 |
| 7 | $CF_3$ | Cl | H | H | Cycloheptyl | H | H | H | I | H | H | H | H | 523 |

EXAMPLES OF PROCESS FOR THE PREPARATION OF THE COMPOUND OF GENERAL FORMULA (I)

Preparation of N-{2-[3-chloro-5-(trifluoromethyl)-2-pyridinyl]-cis-cyclohexyl}-2-(trifluoromethyl)benzamide and N-{2-[3-chloro-5-(trifluoromethyl)-2-pyridinyl]-trans-cyclohexyl}-2-(trifluoromethyl)benzamide (Compound 1 and 2)

1.15 g of 2-[3-chloro-5-(trifluoromethyl)-2-pyridinyl]cyclohexanamine (0.00413 mol), 0.63 ml of triethylamine, 860 mg (0.00413 mol) of 2-trifluoromethylbenzoyl chloride are stirred in 15 ml of dichloromethane at room temperature overnight.

The reaction mixture is concentrated to dryness and purified on silica to yield to 0.66 g of N-{2-[3-chloro-5-(trifluoromethyl)-2-pyridinyl]-cis-cyclohexyl}-2-(trifluoromethyl)benzamide (35%)(mass spectrum : [M+1]=451), and 0.46 g of N-{2-[3-chloro-5-(trifluoromethyl)-2-pyridinyl]-trans-cyclohexyl}-2-(trifluoromethyl)benzamide (25%).

Mass spectrum: [M+1]=451.

Preparation of N-{2-[3-chloro-5-(trifluoromethyl)-2-pyridinyl]cyclohexyl}-2-(difluoromethyl)benzamide (Compound 3)

100 mg of 2-[3-chloro-5-(trifluoromethyl)-2-pyridinyl]cyclohexanamine (0.00036 mol), 62 mg of 2-difluoromethylbenzoic acid, 0.10 g of 4-(4, 6-dimethoxy [1.3.5]triazin-2-yl)-4-methylmorpholinium chloride hydrate (0.00036 mol) are stirred in 2 mL of methanol at room temperature overnight.

The reaction mixture is concentrated to dryness and purified on silica to yield to 31 mg of N-{2-[3-chloro-5-(trifluoromethyl)-2-pyridinyl ]cyclohexyl}-2-(difluoromethyl)benzamide (20%).

Mass spectrum: [M+1]=433.

Preparation of N-{2-[3-chloro-5-(trifluoromethyl)-2-pyridinyl]cycloheptyl}-2-iodobenzamide (Compound 7)

0.35 g of 2-[3-chloro-5-(trifluoromethyl)-2-pyridinyl]cycloheptanamine (0.00119 mol), 0.25 ml of triethylamine, 320 mg (0.0012 mol) of 2-iodobenzoyl chloride are stirred in 2 ml of dichloromethane at room temperature overnight.

The reaction mixture is concentrated to dryness and purified on silica to yield to 0.13 g of N-{2-[3-chloro-5-(trifluoromethyl)-2-pyridinyl]cycloheptyl}-2-iodobenzamide (21%).

Mass spectrum: [M+1]=523.

EXAMPLES OF PROCESS FOR THE PREPARATION OF INTERMEDIATE OF GENERAL FORMULA (II)

Preparation of 2-[3-chloro-5-(trifluoromethyl)-2-pyridinyl]cyclohexanone 10 g (0.05 mol) of 3-chloro-2-fluoro-5-(trifluoromethyl)pyridine and 15.8 g of 1-(1-cyclohexen-1-yl)pyrrolidine (0.105 mol) are stirred neat together at 100° C. for 12 h and 3 days at room temperature.

The reaction mixture is quenched with 100 ml of sulfuric acid 1M. The precipitate which forms is filtered, rinsed with water and air-dried to yield to 10.05 g of 2-[3-chloro-5-(trifluoromethyl)-2-pyridinyl]cyclohexanone (72%).

Mass spectrum: [M+1]=278

Preparation of 2-[3-chloro-5-(trifluoromethyl)-2-pyridinyl]cyclohexanamine 5.0 g (0.018 mol) of 2-[3-chloro-5-(trifluoromethyl)-2-pyridinyl]cyclohexanone are diluted in 25 mL of methanol. 4 g of molecular sieves 4 Å, 13.85 g (0.18 mol) of ammonium acetate and 1.09 g (0.018 mol) of sodium cyanoborohydride are then consequently added.

After 24 h of reaction at room temperature, the medium is filtered, concentrated to dryness and 30 ml of 20% aqueous sodium hydroxide is added.

The aqueous phase is extracted thrice with 100 mL of diethyl ether. The organic phase is dried over magnesium sulfate, filtered and concentrated. The crude material is purified over silica to yield to 2.95 g of desired 2-[3-chloro-5-(trifluoromethyl)-2-pyridinyl]cyclohexanamine (32%).

Mass spectrum: [M+1]=279.

Preparation of 2-[3-chloro-5-(trifluoromethyl)-2-pyridinyl]cycloheptanone 10.07 g (0.05 mol) of 3-chloro-2-fluoro-5-(trifluoromethyl)pyridine and 5.96 g of 4-(1-cyclohepten-1-yl)morpholine (0.015 mol) are stirred neat together at 120° C. for 3 h.

The reaction mixture is quenched with 200 ml of sulfuric acid 5%. The aqueous phase is extracted four times with 100 ml of diethyl ether. The organic phase is dried over magnesium sulfate, concentrated to dryness to yield to 2.53 g of 2-[3-chloro-5-(trifluoromethyl)-2-pyridinyl]cycloheptanone (58%).

Mass spectrum: [M+1]=292.

Preparation of 2-[3-chloro-5-(trifluoromethyl)-2-pyridinyl]cycloheptanamine 2.5 g (0.0086 mol) of 2-[3-chloro-5-(trifluoromethyl)-2-pyridinyl]cycloheptanone are diluted in 25 mL of methanol. 2 g of molecular sieves 4 Å, 6.62 g ( 0.086 mol) of ammonium acetate and 1.14 g (0.017 mol) of sodium cyanoborohydride are then consequently added.

After 24 h of reaction at room temperature, the medium is filtered, concentrated to dryness and 20 ml of 20% aqueous sodium hydroxide is added. 100 ml of ethyl acetate are added, the phases are separated.

The aqueous phase is extracted twice with 50 mL of ethyl acetate. The organic phase is dried over magnesium sulfate, filtered and concentrated to yield to 2.20 g of desired 2-[3-chloro-5-(trifluoromethyl)-2-pyridinyl]cycloheptanamine (88%).

Mass spectrum: [M+1]=293.

EXAMPLES OF BIOLOGICAL ACTIVITY OF THE COMPOUND OF GENERAL FORMULA (I)

Example A

In vivo Test on *Alternaria brassicae* (Leaf Spot of Crucifers)

The active ingredient tested is prepared by potter homogenization in a concentrated suspension type formulation at 100 g/l. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) or total protection is observed at a dose of 330 ppm with the following compounds: 1, 2, 3, 4 and 5.

Example B

In vivo Test on *Erysiphe graminis* f. sp. *tritici*
(Powdery Mildew of Wheat)

The active ingredient tested is prepared by potter homogenization in a concentrated suspension type formulation at 100 g/l. This suspension is then diluted with water to obtain the desired active material concentration.

Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants. Grading is carried out 7 to 14 days after the contamination, in comparison with the control plants.

Under these conditions, good (at least 50%) or total protection is observed at a dose of 330 ppm with the following compounds: 1 and 2.

Example C

In vivo Test on *Pyrenophora teres* (Barley Net Blotch)

The active ingredient tested is prepared by potter homogenization in a concentrated suspension type formulation at 100 g/l. This suspension is then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 50%) or total protection is observed at a dose of 330 ppm with the following compounds: 1, 2, 3, 4, 5, 6 and 7.

The N-{1-methylcarbamoyl-2-[3-chloro-5-(trifluoromethyl)-2-pyridinyl]-ethyl}-4-phenylbenzamide disclosed by Patent Application WO 01/11965 (see compound 316 in Table D) showed poor effectiveness on *Alternaria brassicae*, and zero effectiveness on *Botrytis cinerea* at 330 ppm; the N-{1-ethylcarbamoyl-2-[3-chloro-5-(trifluoromethyl)-2-pyridinyl]ethyl}-3-nitrobenzamide also disclosed by Patent Application WO 01/11965 (see compound 307 in Table D) showed poor effectiveness on *Alternaria brassicae* and zero effectiveness on *Botrytis cinerea* at 330 ppm; the N-{1-ethylcarbamoyl-2-[3-chloro-5-(trifluoromethyl)-2-pyridinyl]-ethyl}-benzamide and the N-{1-methylcarbamoyl-2-[3-chloro-5-(trifluoromethyl)-2-pyridinyl]ethyl}-benzamide also disclosed by Patent Application WO 01/11965 (see compounds 304 and 314 in Table D) showed zero effectiveness on *Botrytis cinerea* at 330 ppm; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by Patent Application WO 01/11965 (see compounds 306, 310 and 315 in Table D) showed zero effectiveness on *Botrytis cinerea* at 330 ppm.

The N-{[3-chloro-5-(trifluoromethyl)-2-pyridinyl]methyl}-5-thienylacetamide disclosed by Patent Application WO 01/11965 (see compound 101 in table B) showed poor efficacy against *Alternaria brassicae* and no efficacy against *Botrytis cinerea* and *Peronospora parasitica* at 330 ppm.

The invention claimed is:
1. A compound of general formula (I):

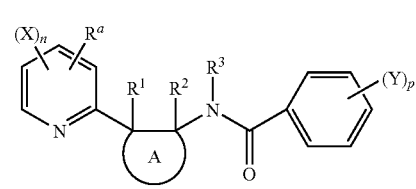

in which:
n is 1, 2, or 3;
p is 1, 2, 3, 4 or 5;
$R^a$ is a fluoroalkyl in 5 position;
X is a halogen atom in 3 position;
A is a 3-, 4-, 5-, 6- or 7-membered non aromatic carbocycle;
$R^1$ and $R^2$ are hydrogen
$R^3$ is selected from the group consisting of hydorgen and $C_1$-$C_6$ alkyl; and
each substituent Y is chosen, independently of the others, as being a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$- halogenoalkoxycarbonyl having 1 to 5 halogen atoms, a alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

as well as its salts, N-oxides, optically active isomers.

2. A compound according to claim 1, characterised in that n is 1 or 2.

3. A compound according to claim 1, characterised in that X is chlorine.

4. A compound according to claim 1, characterised in that $R^a$ is —$CF_3$.

5. A compound according to claim 1, characterised in that the 2-pyridyl is substituted in 3-position by —Cl and in 5-position by —$CF_3$.

6. A compound according to claim 1, characterised in that A is chosen from cyclopropyl, cyclopentyl, cyclohexyl and cycloheptyl.

7. A compound according to claim 1, characterised in that p is 1 or 2.

8. A compound according to claim 1, characterised in that Y is chosen as being a hydrogen atom, a halogen atom, a $C_1$-$C_6$-alkyl, a $C_1$-$C_6$-alkoxy or a $C_1$-$C_6$-halogenoalkyl having 1 to 5 halogen atoms.

9. A compound according to claim 1, characterised in that the phenyl moiety is substituted by Y first in ortho position.

10. A process for the preparation of a compound of general formula (I):

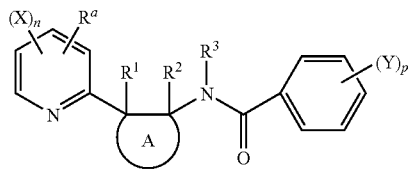

in which:
n is 1, 2, or 3;
p is 1, 2, 3, 4 or 5;
$R^a$ is a fluroalkyl in 5 position;
X is hydrogen atom in 3 position;
A is a 3-, 4-, 5-, 6- or 7-membered non aromatic carbocycle;
$R^1$ and $R^2$ are a hydrogen;
$R^3$ is selected from the group consisting of a hydrogen atom, and $C_1$-$C_6$-alkyl; and
each substituent Y is chosen, independently of the others, as being a hydrogen atom, a halogen atom, a nitro group, a cyano group, a hydroxy group, an amino group, a sulfanyl group, a pentafluoro-$\lambda^6$-sulfanyl group, a formyl group, a formyloxy group, a formylamino group, a carboxy group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkoxy-$C_2$-$C_8$-alkenyl, a $C_1$-$C_8$-alkylsulfanyl, a $C_1$-$C_8$-halogenoalkylsulfanyl having 1 to 5 halogen atoms, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms or a $C_1$-$C_8$-alkylsulfonamide;

as well as its salts, N-oxides, metallic complexes, metalloidic complexes and optically active isomers which preparation process comprises reacting a 2-pyridine derivative of general formula (II) or one of its salts:

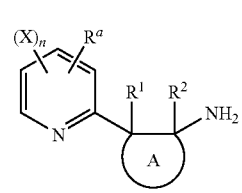

with a carboxylic acid derivative of the general formula (III)

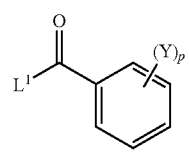

in which:
$L^1$ is a leaving group chosen as being a halogen atom, a hydroxyl group, —$OR^7$, —$OCOR^7$, $R^7$ being a $C_1$-$C_6$ alkyl, a $C_1$-$C_6$ haloalkyl, a benzyl, 4-methoxybenzyl, pentafluorophenyl or a group of formula

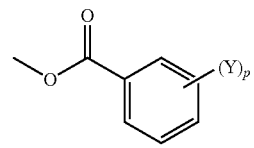

in the presence of a catalyst and, if $L^1$ is a hydroxyl group, in the presence of a condensing agent to form:

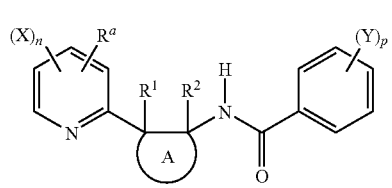

and, if $R^3$ is to be other than hydrogen, conducting a further step of reacting a compound of general formula (Ib) with a compound of general formula XVII to form a compound of general formula (Ia) according to the following reaction scheme:

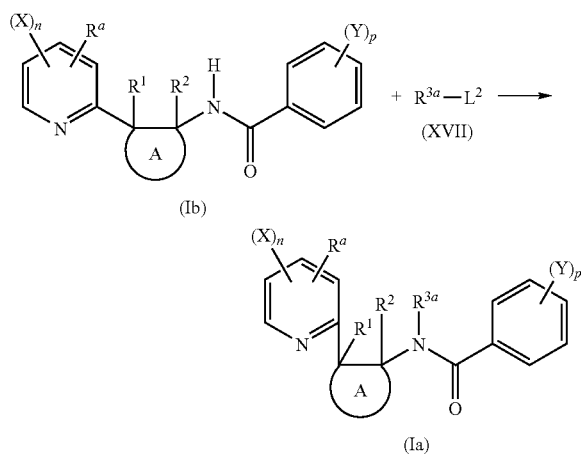

in which:

R³ᵃ is a $C_1$-$C_6$-alkyl; and

L² is a leaving group chosen as being a halogen atom, a 4-methyl phenylsulfonyloxy or a methylsulfonyloxy.

11. A fungicidal composition comprising an effective amount of a compound according to claim 1 and an agriculturally acceptable support.

12. A method for preventively or curatively combating the phytopathogenic fungi of crops, characterised in that an effective and non-phytotoxic amount of a composition according to claim 11 is applied to the plant seeds or to the plant leaves and/or to the fruits of the plants or to the soil in which the plants are growing or in which it is desired to grow them.

* * * * *